United States Patent
Temple et al.

(10) Patent No.: US 9,693,866 B2
(45) Date of Patent: Jul. 4, 2017

(54) TASSELED BONE GRAFT

(71) Applicant: Vivex Biomedical, Inc., Marietta, GA (US)

(72) Inventors: Harry Thomas Temple, Miami, FL (US); Sonya A. Cooper, Miami, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 0 days.

(21) Appl. No.: 14/679,170

(22) Filed: Apr. 6, 2015

(65) Prior Publication Data

US 2016/0151158 A1 Jun. 2, 2016

Related U.S. Application Data

(63) Continuation-in-part of application No. 14/556,492, filed on Dec. 1, 2014, now Pat. No. 9,050,111.

(51) Int. Cl.
| | | |
|---|---|---|
| *A61F 2/28* | (2006.01) | |
| *A61F 2/30* | (2006.01) | |
| *A61L 27/58* | (2006.01) | |
| *A61L 27/36* | (2006.01) | |

(52) U.S. Cl.
CPC .......... *A61F 2/2846* (2013.01); *A61F 2/3094* (2013.01); *A61L 27/365* (2013.01); *A61L 27/3608* (2013.01); *A61L 27/3687* (2013.01); *A61L 27/3691* (2013.01); *A61L 27/3695* (2013.01); *A61L 27/58* (2013.01); *A61F 2002/2839* (2013.01); *A61F 2002/30235* (2013.01); *A61F 2002/30784* (2013.01); *A61F 2210/0004* (2013.01); *A61F 2230/0021* (2013.01); *A61F 2310/00359* (2013.01); *A61L 2430/02* (2013.01)

(58) Field of Classification Search
CPC .... A61F 2/28; A61F 2/44; A61F 2/441; A61F 2/4435; A61F 2002/2828; A61F 2002/2835; A61F 2002/4475; A61F 2002/4495
See application file for complete search history.

(56) References Cited

U.S. PATENT DOCUMENTS

| | | | |
|---|---|---|---|
| 6,290,718 B1 | 9/2001 | Grooms et al. | |
| 7,799,076 B2 * | 9/2010 | Sybert | A61B 17/7062 623/13.17 |

OTHER PUBLICATIONS

Theodore Malinin M.D., H. Thomas Temple M.D. and Arun Garg DMD, "Bone Allografts in Dentistry: A Review".
Carpenter, Ellen M; Gendler, El; Malinin, Theodore I; Temple, H. Thomas; "Effect of Hydrogen Peroxide on Osteoinduction by Demineralized Bone"; The American Journal of Orthopedics, 2006; 35 912 0562-567; Copyright 2006, Quadrant HealthCom Inc.
Temple, H. Thomas; Malinin, Theodore I; "Microparticulate Cortical Allograft: An Alternative to Autograft in the Treatment of Osseous Defects"; The Open Orthopaedics Journal, 2008, 2, 91-96.

* cited by examiner

*Primary Examiner* — Bruce E Snow
(74) *Attorney, Agent, or Firm* — David L. King

(57) ABSTRACT

The present invention relates to a tasseled cortical bone graft and a method of preparing cortical bone in thin strips or tubes then fully demineralizing it to give it formed flexibility and then creating a plurality of strands extending from one or more connection locations in the cortical bone in a fashion similar to a tassel.

5 Claims, 7 Drawing Sheets

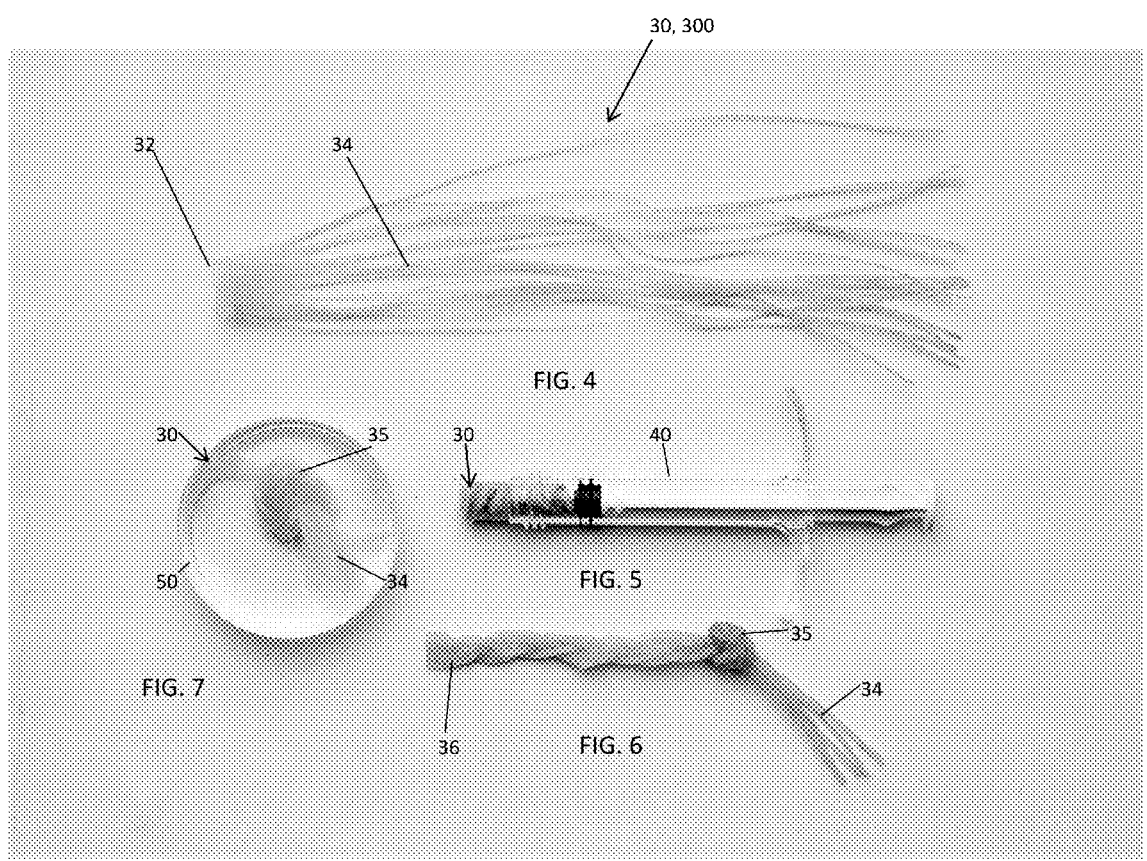

TASSELED BONE GRAFT

RELATED APPLICATIONS

The present invention is a continuation in part of co-pending U.S. application Ser. No. 14/556,492 filed on Dec. 1, 2014 entitled "Fenestrated Bone Graft"; the contents of which are incorporated herein by reference in its entirety.

TECHNICAL FIELD

The present invention relates to a bone graft and a method of preparing fully demineralized cortical bone in thin strips. The bone, being fully demineralized, is pliable which gives it formed flexibility, thereafter creating a plurality of highly flexible elongated tassels or strands extending from one or more connection locations in the cortical bone, creates a tasseled bone graft with at least one connection location.

BACKGROUND OF THE INVENTION

A bone graft is a surgical procedure used to fix problems associated with bones or joints. Bone grafting or transplanting of bone tissue is beneficial in fixing bones after trauma, degenerative damage, problem joints, or growing bone around implanted devices, such as total knee/hip replacement or spinal implants or dental implants. The bone used in a bone graft can come from the patient, from a donor, or could be entirely manmade. Once accepted by the patient, the bone graft provides a framework where new, living bone can grow. The two most common types of bone grafts are allograft: this graft uses bone from a deceased donor or a cadaver that has been cleaned and stored in a tissue bank and autograft: graft made from a bone inside a patient's body, such as the ribs or hips. The type of graft used depends on the type of injury the surgeon will be repairing. Allografts are commonly used in hip, knee, or long bone (arms or legs) reconstruction. The advantages are that (a) there's no additional surgery needed to acquire the bone, and (b) it lowers the risk of infection since additional incisions or surgery on the recipient will not be required. Bone grafting is done for numerous reasons, including injury and disease. There are four main reasons bone grafts are used: fractures, a bone graft may be used in the case of multiple or complex fractures or those that do not heal well after an initial treatment; fusion, most often done in the spine, fusion helps two bones heal together across a diseased joint; regeneration, used for bone lost to disease, infection, or injury, this can involve using small amounts in bone cavities or large sections of bones; and implanted devices, a graft can be used to help bone heal around surgically implanted devices, like joint replacements, plates, or screws.

All surgical procedures involve risks of bleeding, infection, and reactions to anesthesia. Bone grafts carry these and other risks, including: pain, nerve injury, rejection of the bone graft and inflammation. The surgeon typically will make an incision in the skin above where the graft is needed. He or she will then shape the donated bone to fit the area. The graft will be held in place using various pins, plates, or screws.

The present invention provides a new and improved type of bone graft and a method of manufacturing the graft to facilitate improved implantation techniques.

SUMMARY OF THE INVENTION

The present invention relates to a tasseled cortical bone graft and a method of preparing cortical bone in thin strips or thin tubes then fully demineralizing it to give it formed flexibility and then creating strands or tassels extending from one or more connection locations in the cortical bone.

The advantage of this new allograft is it provides a unique way to develop ingrowth through the strands. The strips can be cut up to 30 cm so they can be used for lateral lumbar fusions or even multiple fusions in the thoracic and lumbosacral spine. The graft can also be wound and rolled or compacted into a construct that can be used inside of a cage. The flexibility also allows for the ability to create different shapes such as a tube or a basket that can contain either allogeneric or autogeneric or combinations thereof of bone graft material with or without stem cells. The tasseled bone graft is relatively inexpensive and easily scaled. The tasseled bone graft is a device in which the tassels allow for the use weaved or braided material made from the same bone that can be used to create a variety of shapes.

Preferably, a tasseled cortical bone graft has an allograft bone structure. The allograft bone structure has one or more connection locations and a plurality of strands or tassels. The allograft bone structure can be formed as a flat sheet. Alternatively, the allograft can be formed as a tubular or cylindrical shaped graft. The allograft bone structure is preferably made pliable. The pliable allograft bone structure is conformable to flex about the surface of a damaged bone to provide a tasseled cortical bone graft.

DEFINITIONS

As used herein and in the claims:

"BMA" refers to Bone Marrow Aspiration, a technique used to obtain the blood-forming portion (marrow) of the inner core of bone for examination in the laboratory or for transplantation.

"Costal cartilage" refers to the cartilages that connect the sternum and the ends of the ribs; its elasticity allows the chest to move in respiration.

Demineralized bone matrix (DBM) is an osteoconductive and osteoinductive commercial biomaterial and approved medical device used in bone defects with a long track record of clinical use in diverse forms. True to its name and as an acid-extracted organic matrix from human bone sources, DBM retains much of the proteinaceous components native to bone, with small amounts of calcium-based solids, inorganic phosphates and some trace cell debris. Many of DBM's proteinaceous components (e.g., growth factors) are known to be potent osteogenic agents. Commercially sourced as putty, paste, sheets and flexible pieces, DBM provides a degradable matrix facilitating endogenous release of these compounds to the bone wound sites where it is surgically placed to fill bone defects, inducing new bone formation and accelerating healing. Given DBM's long clinical track record and commercial accessibility in standard forms and sources, opportunities to further develop and validate DBM as a versatile bone biomaterial in orthopedic repair and regenerative medicine contexts are attractive.

"PRP" refers to platelet-rich plasma which is blood plasma that has been enriched with platelets. As a concentrated source of autologous platelets, PRP contains and releases through degranulation several different growth factors and other cytokines that stimulate healing of bone and soft tissue.

The term "Tassel" means a plurality of long strands extending from at least one connection location.

BRIEF DESCRIPTION OF THE DRAWINGS

The invention will be described by way of example and with reference to the accompanying drawings in which:

FIG. 4 shows a tasseled cortical bone graft.

FIG. 5 shows a tasseled cortical bone graft compacted into a syringe.

FIG. 6 shows a tasseled cortical bone graft braided and knotted.

FIG. 7 shows a tasseled cortical bone graft wound and knotted.

DETAILED DESCRIPTION OF THE INVENTION

Figure 1:
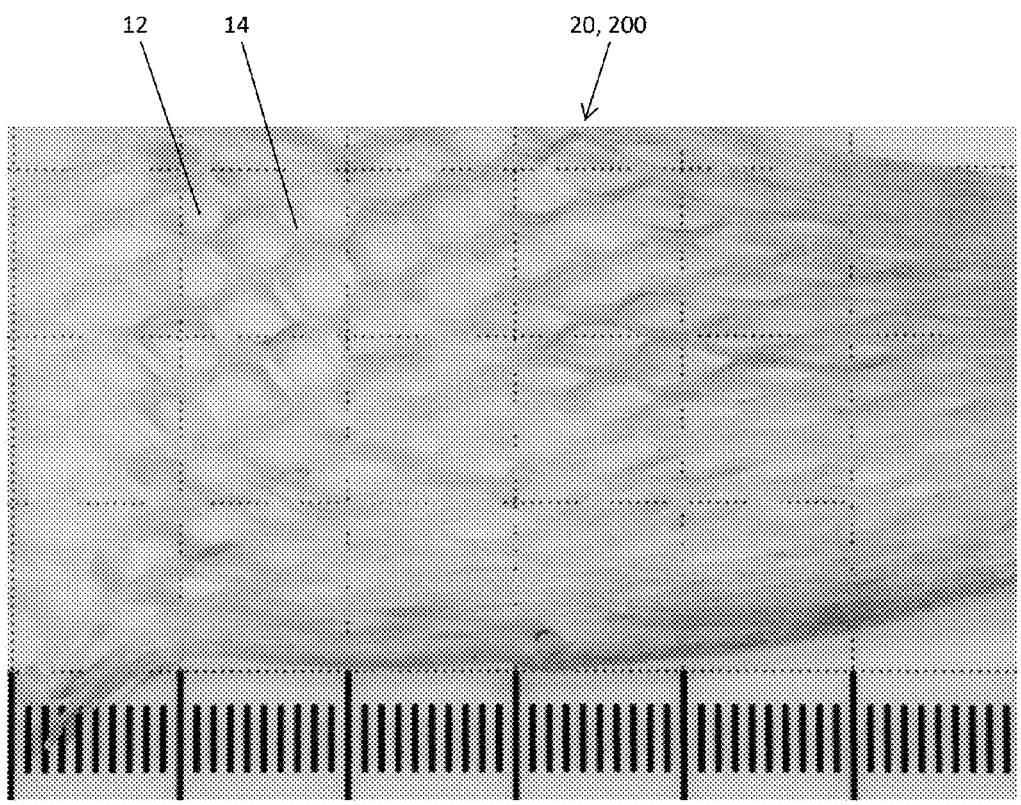
FIG. 1 shows 15-20 cm cortical demineralized graft with fenestrations, Freeze dried. Clinical usage for long segment fusion, segmental defects as a wraparound intramedullary implant.
Figure 2:
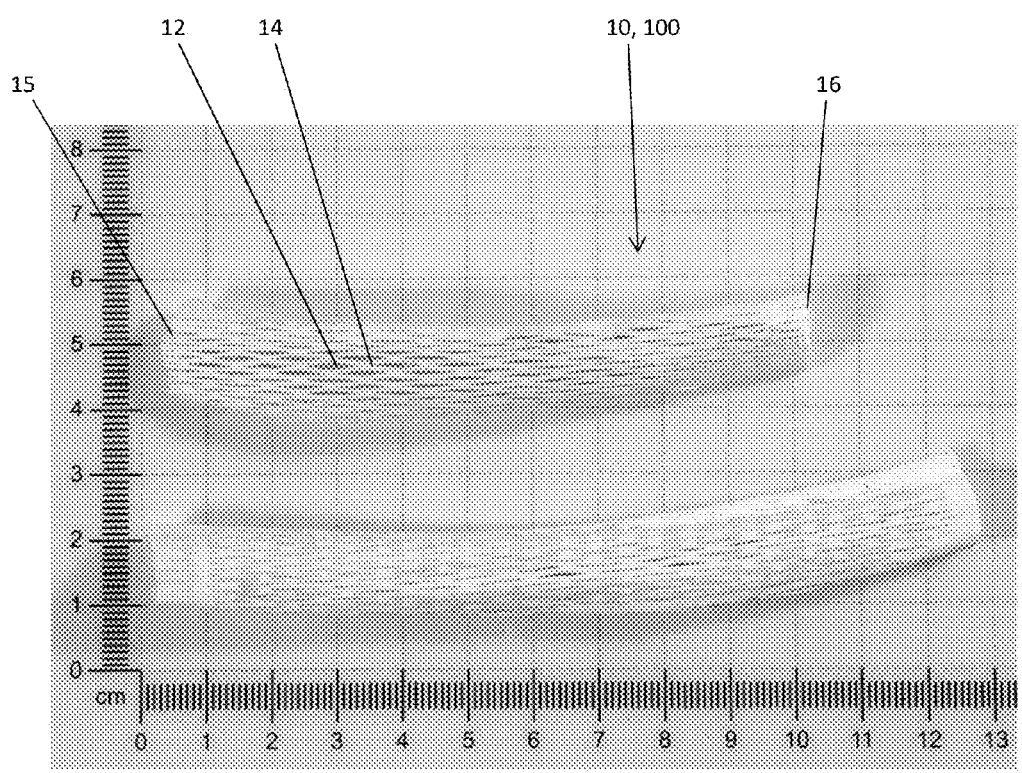
FIG. 2 shows Rib with fenestrations. Clinical indications, cranio and maxillofacial surgery, spinal cage filler (can add micronized bone, DBM, MIAMI cells) to intact center.
Figure 3:
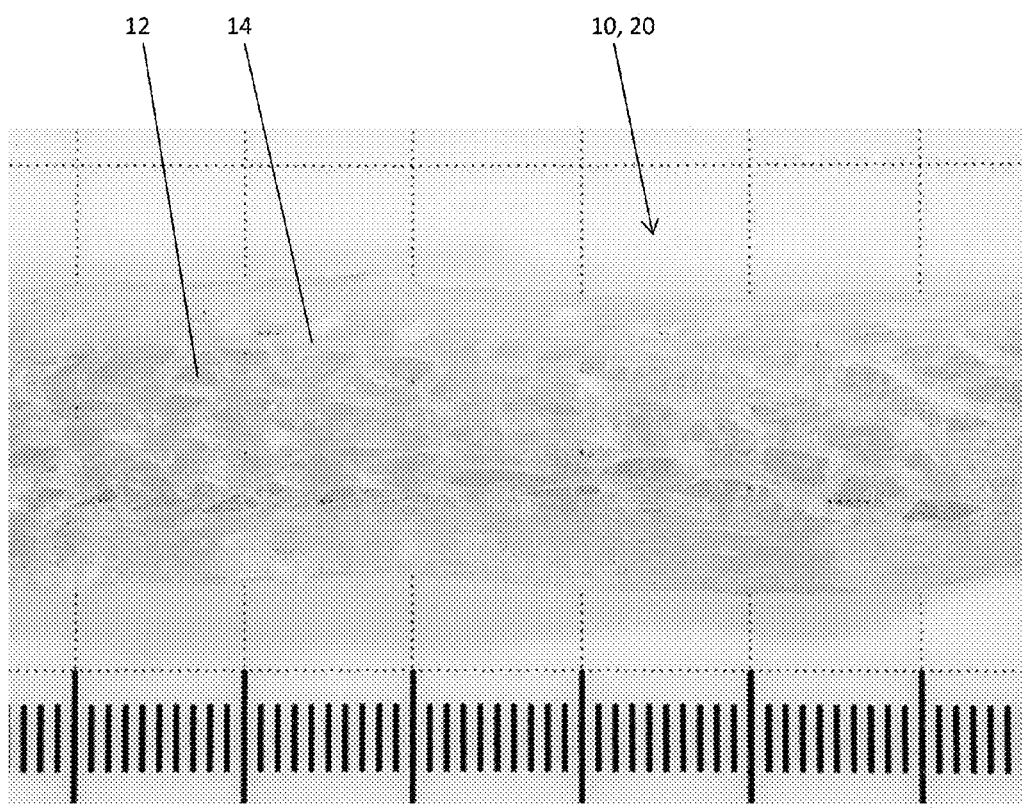
FIG. 3 shows Demineralized rib; higher power magnification demonstrating fenestrations and cortical architecture.

As shown in FIGS. 1-3, the original concept taught in co-pending application Ser. No. 14/556,492 filed on Dec. 1, 2014, of fenestrating demineralized cortical bone was developed in the rib 100 and the rib 100 was an ideal graft because it can essentially be demineralized and creates a large wide flat surface. The cancellous center may or may not be removed after which the rib 100 is passed through a press with cutting or punch blades that create fenestrations or openings 12 bounded by interconnected bone struts 14 that gave the fenestrated bone graft 10 a porosity as well as stretchability and flexibility to fit into relatively defined spaces. The actual preparation of the rib graft may be done aseptically or use alcohols, peroxides or decontamination steps in its processing. In doing so, the clinicians removed all of the costal cartilage that they used for other applications and distribution. They cut the rib 100 at ends 15, 16 into relatively long segments at least greater than 5 cm. Following that, they treated the graft for a predetermined time in 1N HCL (one normal hydrochloric acid) (20-50 parts/gram) ranging from approximately 1-24 hours continuously inspecting the graft rigidity. Once they were satisfied with the texture and flexibility of the graft 10 they washed it in a washing solution of Phosphate buffered saline approximately 20 minutes. Then they cut the rib 100 longitudinally to maintain its cylindrical configuration. This cut along the length allowed for either using the graft as a flat construct or it could maintain the graft 10 in a cylinder. The fenestration portion of the graft 10 was cut into the rib 100 and created using an in-house made bone cutter. Once the fenestrations or openings 12 were made in the graft 10, the graft 10 was freeze dried using an overnight cycle and then packaged sterilely for clinical use in a peel pouch. Following the removal of the graft 10 from the plastic peel pouch it can be reconstituted in saline or lactated ringers with or without antibiotics for clinical applications. The graft 10 could be refolded into a cylindrical configuration and filled with either autologous or allogenic bone graft with or without stem cells moreover the graft 10 could be rolled or folded into a confined space such as a cage or rolled into a cylinder where it could be used for the application of satisfying a short close open segment defect. The graft 10 could also be onlaid into a vascularized myo-osseous pouch for the purpose of long segment fusions in the spine, the thoracic or lumbosacral spine.

The tibial graft 20, as shown in FIG. 1, was conceived to create longer segments of bone for very long segment fusions in the case of scoliosis or a multi-segment instability or trauma of the spine. Again the graft 20 was recovered from a tibia 200, in aseptic fashion with or without the use of peroxides, detergents or secondary decontamination steps. Secondary sterilization could however be employed if cultures were positive for non-exclusionary organisms as outlined in FDA guidelines. Aseptic cleaning in the processing state has been reinstituted and the tibia graft 20 was cut on a band saw in a coronal fashion in lengths 10 cm or greater, while the thickness is approximately 0.2 to 1.5 mm. The graft 20 was then placed in a large graft cylinder and treated with 1N HCL (20-50 parts/gram) for 3-24 hours with continuous inspection to assess the rigidity and texture of the graft 20. Once the appropriate texture was obtained, it was then washed in phosphate buffered saline three separate times for 20 minutes. The graft 20 was then placed on the bone cutter to create the appropriate fenestrations or opening 12 bound by the interconnected bone struts 14 and then the tibia graft 20 was placed in the freeze drier for an overnight cycle. It was then packaged sterilely for clinical use. In using the tibia graft 20, it was removed from the peel pouch and reconstituted in saline or lactated ringers with or without the addition of antibiotics and then depending on the particular application, the tibia graft 20, like the rib graft 10 would be onlaid or folded into a cylinder or a roll or a basket into which particulate graft could be added along with a stem cell. The indications for this graft 20 are felt to be long segment fusion such as scoliosis, multi-level and trauma as well as maxillofacial surgery, surgery involving defects in cranial pulp, or long segment defects as well as any other defect.

FIG. 1 is essentially showing a portion of a 20 cm long fenestrated bone graft 20 that was derived from the tibia 200. It is freeze dried and this is done after the fenestrations 12 were created in the graft after it was fully demineralized. Once this fenestrated bone graft 20 is hydrated it resumes its pliable shape and can be formed into several alterations that can retain smaller bone particulate graft and stem cells.

FIG. 2 shows a cylindrical graft 10 made from rib 100. One notes that the fenestrations 12 are created by not having to longitudinally section the rib 100, but using a more robust cut to create fenestrations 12 throughout the graft 10. This is a very interesting graft because it can be filled with allograft bone particulate graft or dbm or stem cells or a combination thereof and can be sewn or restricted above and below at ends 15, 16 of the rib graft 10. This construct can be used to fill a cage construct or potentially to augment a segmental defect or to satisfy a defect in the portion of a long bone or a strip in a pelvis.

FIG. 3 is a higher power magnification showing the morphologic changes that are created in the demineralized cortical bone following fenestration. One notes the uniformity and openness of porous bone structure and the intervening connective strut structure 14 of cortical bone.

The desired texture is a surface related property that has to do with the pliability and stretchability of the grafts 10, 20 themselves. It has to be sufficiently demineralized to have the flexibility which allows creating a variety of different shapes. If too stiff, obviously it can't create these shapes, if demineralized it too much it loses some of the inductivity that is inherent in demineralized bone.

With reference to the present invention shown in FIGS. 4-12, the cortical bone is initially prepared exactly the same way as previously described and shown in FIGS. 1-3 for the rib 100 or tibia 200, however, instead of creating fenestrations, the rib 100 or tibia 200 or whatever long bone is selected has a connection location 32 maintained and a plurality of longitudinally cut strands 34 extending from the connection location 32 along the entire length to form a tasseled cortical bone 30 as illustrated in FIG. 4. This can also be prepared from a femur 300. The allograft bone structure when made from one long bone forms a single piece unitary structure.

The strands 34 are cut lengthwise to create very flexible strands 34. Each strand 34 is integral to the connection location 32, but separated from the other strands 34 along their length.

As shown in FIGS. 5, 6 and 7, the strands 34 can be braided 36 or tied in a knot 35 to form a 3 dimensional mass of bone material for implantation. The strands 34 in FIG. 7 are twisted or wound then a knot 35 is tied about midway on the tassel 30.

In FIG. 5, the tassel 30 is packed inside a syringe 40 for implantation. As shown, the partially exposed tasseled bone graft 30 maintains the cylindrical shape of the inside of the syringe 40 as it is pushed out. This ability to conform in shape makes it ideal for implantation.

The tasseled bone graft 30 when made from demineralized cortical bone that is made into strands 34 then braided 36 or wound into compact structures is very osteoinductive and can be used as a lateral gutter fusion, cage fusion, braided for ACL reconstruction, cranial defects and sinus reconstruction in dentistry.

Figure 8:
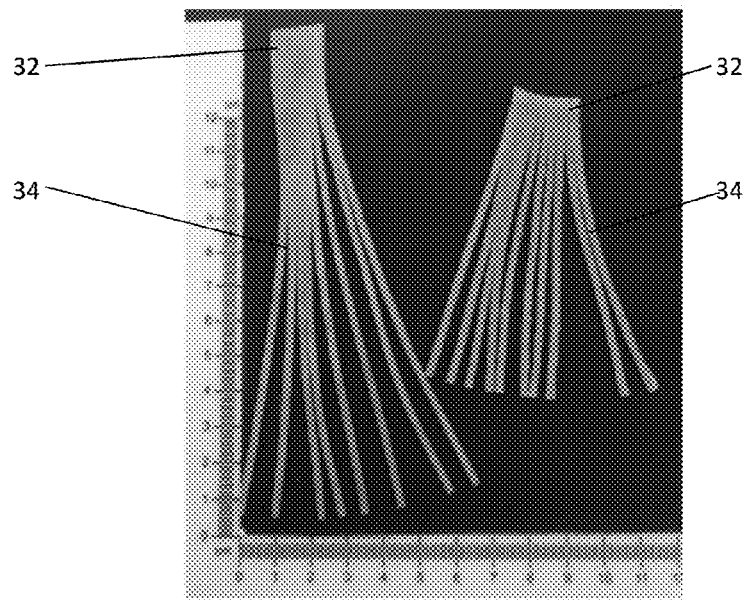
FIG. 8 shows a pair of tasseled cortical bone graft on a scale.

In order for new bone to form, three critical elements are required: osteoconductive scaffold, or a surface for bone to grow on, in and through; osteogenic cells, the cells that produce bone; and osteoinductive signals, proteins/molecules that tell the cells what to do. With reference to FIG. 8, two embodiments are shown on a scale. One being from a tibia 200, the other being from a rib 100. The invention exhibits the following features: 100 percent human demineralized cortical bone; fenestrated to create a surface for bone to grow on, in and through; unique one unit tassel design allows to solve the common problems of graft site migration and the ability to visualize the implant post-surgery; demineralized bone fibers support osteogenesis and osteoconduction; cortical sheets are machine stamped for consistency; flexible handling characteristics; osteoconductive; osteoinductive properties; easy to handle and deliver, pre-configured implant sized to the specific procedure; easily cut to size with scissors or scalpel; available in multiple sizes; 5 year shelf life; room temperature storage; packaged in packs of 20 for single use (10 per side-min).

The invention has the following benefits: utilizing this demineralization technology, the grafts are flexible and feature osteoinductive and osteoconductive properties; when combined with blood, PRP, BMA the graft provides all of the necessary elements for bone regeneration; easily cut and shaped for various defect sizes, it has a unique malleability that helps in placement; following hydration it can be folded, rolled, trimmed, and/or sutured making it an ideal scaffold which will remodel and function like bone in the defect; can be sutured in place.

Figures 9A, 9B, 9C:
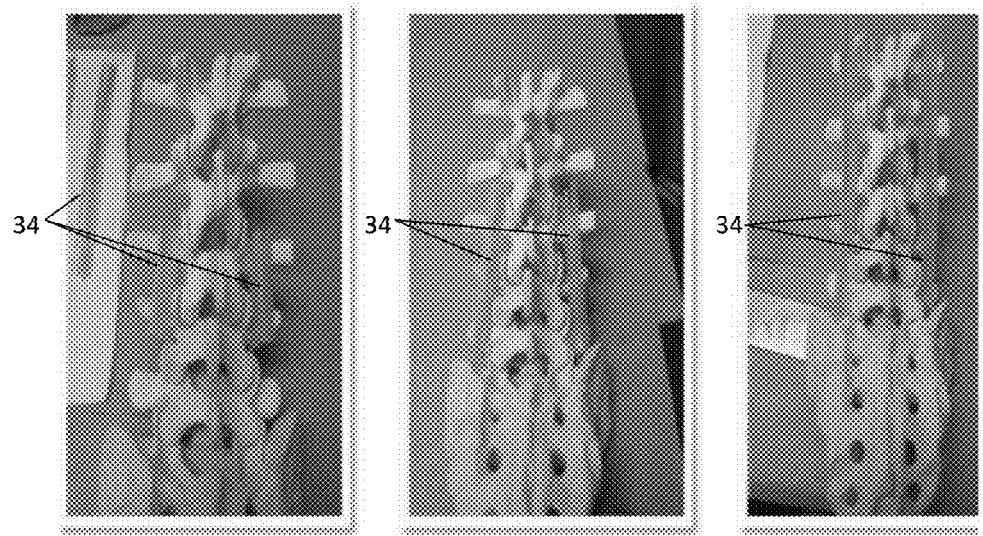
FIG. 9A, 9B, 9C shows the onlaid tasseled cortical bone graft in a spine repair.
Figure 10A:
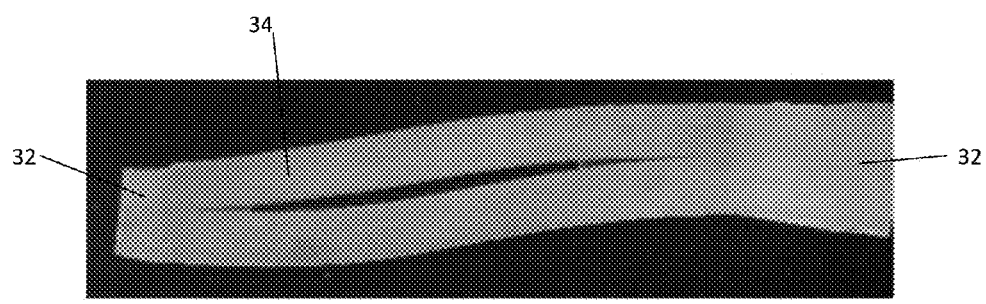
FIG. 10A shows a double ended tasseled cortical bone graft flat.
Figure 10B:
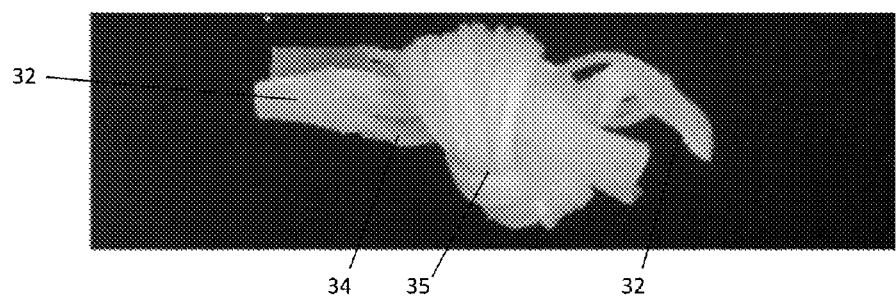
FIG. 10B shows a double ended tasseled cortical bone graft knotted.
Figure 11:
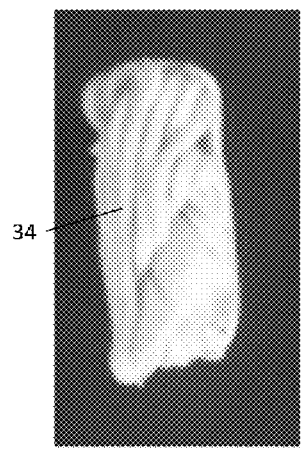
FIG. 11 is a packed tasseled bone graft.
Figure 12:
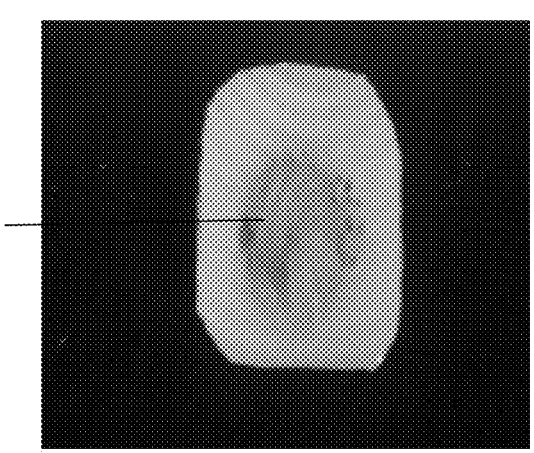
FIG. 12 is a wound tasseled bone graft.

Alternatively, as shown in FIGS. 9A-9C, the connection location 32 which conveniently holds the strands 34 together could be cut or removed leaving the strands 34 as separate pieces that could be tied, wound or braided in the absence of the connection location 32. As illustrated in FIGS. 9A-9C, the strands 34 are designed for posterolateral spine surgery applications, including single and multi-level fusions, as well as deformity procedures. The tassel is a single unit when formed with a connection location, but when implanted with the connection location cut away, it can have at least twice the fiber strands for minimal graft migration or washing out with irrigation, as shown.

Figure 13:
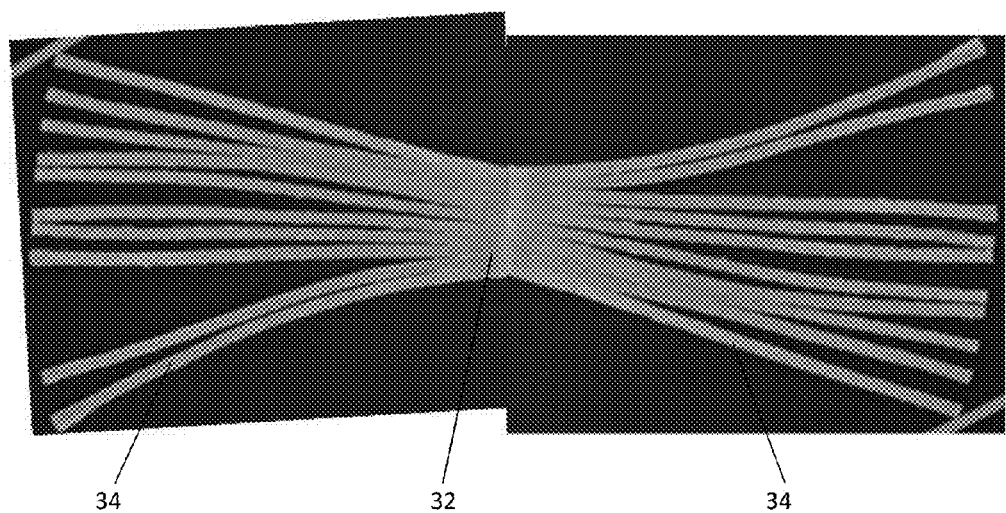
FIG. 13 is a tasseled bone graft with the connection location in the center with tassels on each end.

Also, the connection location 32 could be relocated, for example midway along the bone where the tassels would be formed on each side of the connection location 32 as shown in FIG. 13.

The individual strands 34, when cut, have an almost square cross section, the cross sectional shape can be an arcuate segment or a wider rectangular profile. The main point is the strands 34 need to be long and flexible. When constructed as taught, the cross section can be preferably about 0.5 to 4.0 mm, preferably about 0.5-2.0 mm wide and of a similar thickness. The strands 34 when so constructed, are very strong and yet somewhat elastic and able to stretch before breaking allowing them to be braided or tied without fracturing.

As shown in FIGS. 10A, 10B, 11 and 12, units with many fibers, appearance like a "bird's nest" for extraordinary wicking and minimal graft migration or washing out with irrigation. As further illustrated, the connection locations 32 from which the strands 34 extend can be provided at both ends as another alternative.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A tasseled cortical graft consists of:
an allograft bone structure made from one cortical long bone, the allograft bone structure being a single piece unitary structure having only one connection location formed as a solid section of the bone and a plurality of straight strands integral to and extending along a length from the one connection location, each straight strand being integral to the one connection location, each straight strand being formed by two straight line cuts extending along either side of the entire length of each strand from the one connection location and separating each straight strand from other straight strands along the length of the allograft bone structure from the one connection location wherein all said strands are joined and integral to said connection location, and
wherein the one connection location is midway and the tassels are formed on each side of the one connection location.

2. The tasseled cortical graft of claim 1 wherein the allograft bone structure is formed as a flat sheet.

3. The tasseled cortical graft of claim 1 wherein the allograft bone structure is made pliable.

4. The tasseled cortical graft of claim 3 wherein the allograft bone structure is conformable about the surface of a damaged bone to provide a tasseled cortical bone graft.

5. The tasseled cortical graft of claim 1 wherein the bone structure is a bone including one of a rib, a tibia, a femur.

* * * * *